United States Patent
Busolin et al.

(10) Patent No.: US 10,420,354 B2
(45) Date of Patent: *Sep. 24, 2019

(54) COMPOSITION OF A CONFECTIONERY PRODUCT

(71) Applicant: ROQUETTE FRERES, Lestrem (FR)

(72) Inventors: Andre Busolin, Ornex (FR); Antoine Barre, Saint-Andre-lez-Lille (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,304

(22) PCT Filed: Jul. 1, 2015

(86) PCT No.: PCT/FR2015/051817
§ 371 (c)(1),
(2) Date: Dec. 30, 2016

(87) PCT Pub. No.: WO2016/001586
PCT Pub. Date: Jan. 7, 2016

(65) Prior Publication Data
US 2017/0135370 A1    May 18, 2017

(30) Foreign Application Priority Data

Jul. 1, 2014    (FR) ...................... 14 56288

(51) Int. Cl.
A23G 4/10 (2006.01)
A61K 47/26 (2006.01)
A61K 9/68 (2006.01)

(52) U.S. Cl.
CPC .............. *A23G 4/10* (2013.01); *A61K 9/0058* (2013.01); *A61K 47/26* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,661,647 A * | 4/1987 | Serpelloni | ............ | A61K 9/2018 422/254 |
| 5,139,795 A * | 8/1992 | DuRoss | ................. | A23G 3/346 127/29 |
| 6,630,586 B1 | 10/2003 | Fouache et al. | | |
| 7,300,679 B1 * | 11/2007 | Robinson | ............... | A23G 3/346 127/30 |
| 8,652,513 B2 | 2/2014 | Lefevre et al. | | |
| 2012/0156496 A1 * | 6/2012 | Boit | ........................ | C07C 29/78 428/402 |
| 2013/0149412 A1 * | 6/2013 | Reed | ....................... | A23G 4/10 426/3 |
| 2013/0177668 A1 * | 7/2013 | Fuchs | ..................... | A23G 3/346 426/3 |
| 2013/0302387 A1 | 11/2013 | Pedersen | | |

FOREIGN PATENT DOCUMENTS

| | | | |
|---|---|---|---|
| EP | 0 347 121 A2 | 12/1989 | |
| EP | 1 006 128 A1 | 6/2000 | |
| FR | 1 456 288 A | 11/1965 | |
| WO | 2005/060944 A1 | 7/2005 | |
| WO | WO 2012122013 A2 * | 9/2012 | ............. A23G 4/064 |

OTHER PUBLICATIONS

Horiba Scientific. Understanding and interpreting particle size distribution calculations. Downloaded Jun. 18, 2018 from http://www.horiba.com/scientific/products/particle-characterization/education/general-information/data-interpretation/understanding-particle-size-distribution-calculations/ (Year: 2018).*
Rowe et al.:"Handbook of Pharmaceutical excipients 7th Edition", Jan. 1, 2012, Pharmaceutical Press, article "Handbook of Pharmaceutical excipients 7th Edition", pp. 479-482, XP055217505.
Anonymous: "Sucre glace—Wikipedia", May 28, 2014 (May 28, 2014), XP055217333, Retrieved from the Internet <URL:https://fr.wikipedia.org/w/index.php?title=Sucre_glace&oldid=104173601> [retrieved on Sep. 30, 2015].
S. Brunauer et al., Journal of American Chemical Society, vol. 60, 1938, pp. 309.
International Search Report, dated Oct. 9, 2015, from corresponding PCT application.

* cited by examiner

*Primary Examiner* — Michael P Cohen
(74) *Attorney, Agent, or Firm* — Oliff PLC

(57) ABSTRACT

A novel composition of a confectionery or pharmaceutical product, characterized in that it includes 30 to 70 wt % of a bulking agent other than maltitol having a specific surface area smaller than 0.5 m2/g and also having a reduced amount of base gum, with no negative effect on the organoleptic properties, relative to the prior art products. Also, a method for using the novel composition in the production of a chewing gum characterized in that it enables the amount of base gum in said products to be considerably reduced.

10 Claims, No Drawings

COMPOSITION OF A CONFECTIONERY PRODUCT

FIELD OF THE INVENTION

The invention relates to a novel composition of a confectionery or pharmaceutical product, characterized in that it comprises between 30% and 70% by weight of a bulking agent other than maltitol having a specific surface area of less than 0.5 m$^2$/g and also having a reduced amount of gum base, with no negative effect on the organoleptic properties, compared with the prior art products. The invention also relates to the process for using said composition in the production of a chewing gum, characterized in that it makes it possible to considerably reduce the amount of gum base of said products.

TECHNICAL BACKGROUND

Man has known about chewing for a very long time, long before the arrival of chewing gum. Indeed, prehistoric man already used to chew conifer sap, leaves, plant secretions and roots. In Mexico, the Mayans, more than 3000 years ago, used to chew sapodilla sap, a kind of latex known as "chicle". In 400 BC, the Greeks used to chew resin, and the Amazonian Indians chewed balls of tobacco or wads of coca extracted from small Peruvian shrubs: the cola tree.

However, it was not until the 19th century that chewing gum as we know it today appeared.

In 1869, the patent for chewing gum was filed by the dentist William Finley Semple, who was convinced of its beneficial effects for the teeth, but he did not market his invention. It was in about 1870 that Thomas Adams of New York had the idea of developing a machine for producing chewing gum. By mixing chicle, resin and syrup, he produced and marketed the first chewing gums in 1872.

Today, France has become the 2$^{nd}$ worldwide consumer of chewing gum, behind the United States. Chewing gum can be consumed at any time of the day. It is the ideal product when a person wishes to consume something pleasant or to eat something sweet. Furthermore, irrespective of its flavor, chewing gum makes the breath fresh and plays a hygiene and social role. 53% of people chew chewing gum to freshen their breath. Chewing gum is increasingly appearing as a substitute for toothpaste. 39% of people chew chewing gum to clean their teeth when they cannot brush them. Chewing gum is in particular consumed after meals since it facilitates digestion by promoting the secretion of saliva and the work of the stomach. Many consumers use chewing gum as an anti-stress agent or as a means for reducing nervous tension and for relaxing. 30% of individuals like chewing gum when they are irritated and 27% become calm on chewing chewing gum. Chewing gum is also considered to be an effective substitute for smoking. In a time when the legal measures directed toward reducing tobacco consumption are on the strong increase, chewing gum still has ripe perspectives for development.

Chewing gum (or chewing gum paste, chiclette) is a gum to which are added flavorings and food fragrances, intended to be chewed. All chewing gums are produced from a gum base to which are added flavorings and sugar and/or sweeteners to give the taste. Chewing gum is a mixture of two phases: a liquid phase (syrup, diluted sugars and/or sweetener) and a solid phase composed of the gum base and granulated sugar and/or sweetener.

At the current time, chicle, a natural gum base derived from the trunk of sapodilla trees, but which has become too expensive due to the rarity of the trees and the excessively high production and transportation costs), has been replaced with a synthetic product (gum base) which is composed of:
1 or 2 elastomers that determine the elasticity,
waxes which lower the softening point and which have an anti-tack and plasticizing power,
mineral bulking agents which improve the mechanical qualities,
an antioxidant which protects the qualities of the gum during production and which protects it from aging,
resins which bind together the raw materials of the gum.

The dosage of these 5 ingredients determines the type of gum (chewing gum or bubble gum). The recipe often remains secret because it is not constant. It varies according to the price of the raw material. The constituent ingredients of the gum base are water-insoluble. On the other hand, the majority of the constituent ingredients of chewing gums, except for the gum base, are soluble in water (i.e. in this case saliva). After 3 to 4 minutes of chewing time, the compounds are extracted (dissolved) by the saliva, hence the loss of taste of the chewing gum. The gum base and a few flavorings that are not water-soluble remain in the mouth.

The gum base is a product that is complex to produce: the ingredients are meted out rigorously to obtain more or less elastic gums. The ingredients are blended for between one and a half hours and two hours in a kneader which operates like bakery kneaders. The blending heats the gum. It finally reaches a temperature of 95° C. to 98° C. The elastomer used (in place of the chicle) is a food-quality isobutylene-isoprene (butyl) copolymer.

The flavorings, sweeteners or sugar and also various additives and production aids (colorant, gelatin, emulsifier, stabilizer, gelling agent, bicarbonate, carnauba wax) are added to this base. The ingredients and the gum base are mixed in a kneader for 15 to 20 minutes. At the end of blending, the paste reaches a temperature of approximately 50° C. The chewing gum paste is placed in an extruder. Once correctly pressed, it then forms more or less thick strips. The strips then pass through the roller and are cut into sticks or cores also known as centers. After cooling, the sticks or centers are maintained at a control temperature and humidity for 6 to 48 hours. This phase is carefully controlled, since the quality of the chewing gums is dependent thereon.

The sticks are wrapped in an aluminum wrapping to conserve all their taste. They are then placed in packets. The centers are sweet-coated before being packaged in cardboard or plastic containers.

Irrespective of the age of the consumers, there is a permanent desire to have quality products. The quality of chewing gums is measured by several parameters, including the texture of the chewing gum (rather hard or, on the contrary, rather soft, persistent crunchiness of the sweet-coated tablets during chewing) and the taste (sweet taste, freshness effect or otherwise, persistence of the flavor during chewing). Indeed, consumers very often complain that both the crunchiness and the taste disappear too quickly during chewing.

Furthermore, with a permanent desire to reduce costs, manufacturers constantly seek improvements in their already existing recipes without, however, having an impact on the organoleptic qualities of the final products. These cost reductions that are sought involve for example the reduction of expensive ingredients, such as the gum base and/or the amount of flavoring used.

Numerous research studies have already been carried out on the persistence of the taste by numerous companies. The applicant has also worked on this subject and mention may be made in this respect of patent EP 0 664 960 B in which the applicant demonstrated that it was possible to improve the organoleptic property of a chewing gum, and in particular to improve the taste and flavor in terms of impact and duration, by incorporating therein, as pulverulent phase, maltitol with a maltitol purity of greater than 95% and a particle size such that 50% of the maltitol particles in the chewing gum are less than 90 microns in size.

In wishing to further improve upon the prior art and especially to satisfy the ever more demanding expectations of consumers, the applicant thus sets itself the task of obtaining a novel chewing gum having all the desired characteristics with a reduced amount of gum base in the final product, with no impact on the organoleptic properties, and in particular on the chewing volume and/or on the aromatic note perceived during chewing by consumers.

SUMMARY OF THE INVENTION

After numerous research studies, the applicant has found that, surprisingly and unexpectedly, it is possible to obtain a chewing gum which has all the organoleptic characteristics of a prior art chewing gum, by using a bulking agent other than maltitol which has a particular specific surface area and, preferably, a given porosity.

The use of this quite particular bulking agent makes it possible, inter alia, to reduce the amount of gum base used in the processing of the chewing gum compositions.

Thus, the invention relates to a chewing gum composition characterized in that it comprises between 30% and 70% by weight of a bulking agent other than maltitol which has a specific surface area, determined by the BET method, of less than 0.5 $m^2/g$, preferably of between 0.2 and 0.45 $m^2/g$, and preferably between 0.1 and 0.3 $m^2/g$, said specific surface area being measured on a fraction from 250 μm to 841 μm.

According to the invention, this chewing gum composition is also characterized in that the bulking agent preferably has a porosity of less than 0.0085 ml/g, preferably less than 0.0080 ml/g and even more preferentially less than 0.0070 ml/g.

Said bulking agent is between 30% an 70%, preferably between 40% and 60%, and even more preferentially between 45% and 55% in the chewing gum composition according to the invention, the percentages being expressed by weight relative to the total weight of the chewing gum composition used.

Still according to the present invention, said composition is also characterized in that the bulking agent other than maltitol is a pulverulent composition chosen from non-cariogenic carbohydrates, and/or fibers and/or monosaccharides and/or any mixtures thereof, preferably from non-cariogenic carbohydrates, and even more preferentially from polyols and/or allulose and/or any mixtures thereof.

According to one embodiment of the invention, the chewing gum composition comprises a bulking agent chosen in particular from the group comprising sorbitol, xylitol, erythritol, isomalt, isomaltitol, lactitol, alpha-D-glucopyranosyl-1,6-sorbitol (=1,6-GPS), alpha-D-glucopyranosyl-1,1-maltitol (=1,1-GPM), alpha-D-glucopyranosyl-1,1-sorbitol (=1, 1-GPS) and mixtures thereof.

Preferably, said bulking agent is sorbitol, more preferentially having a purity greater than 95% by dry weight of sorbitol.

The chewing gum composition according to the invention comprises:
 from 10% to 28%, preferentially from 15% to 25%, and even more preferentially 20%, of at least one gum base,
 from 30% to 70%, preferably from 40% to 60%, and even more preferentially from 45% to 55%, of a bulking agent other than maltitol which has a low specific surface area, i.e. less than 0.5 $m^2/g$, measured on a fraction from 250 μm to 841 μm,
 from 0.1% to 5%, preferentially from 0.5% to 3%, and even more preferentially from 1% to 1.8%, of at least one flavoring,
the percentages being indicated by dry weight relative to the total dry weight of said composition.

Finally, the invention also relates to the use of a bulking agent other than maltitol which has a specific surface area, determined by the BET method, of less than 0.5 $m^2/g$, preferably of between 0.2 and 0.45 $m^2/g$, and preferably between 0.1 and 0.3 $m^2/g$, said specific surface area being measured on a fraction from 250 μm to 841 μm, in the production of chewing gums and/or in the production of tablets for pharmaceutical or food use.

DETAILED DESCRIPTION OF THE EMBODIMENTS

The present invention relates to a novel chewing gum composition characterized in that said chewing gum composition comprises between 30% and 70% by weight of a bulking agent other than maltitol which has a specific surface area, determined by the BET method, of less than 0.5 $m^2/g$, preferably of between 0.2 and 0.45 $m^2/g$, said specific surface area being measured on a fraction from 250 μm to 841 μm.

Throughout the present invention, it will be considered that all the percentages expressed, unless explicitly otherwise mentioned, are expressed relative to the total weight of the chewing gum composition used.

The specific surface area of a powder corresponds to the developed surface per unit of mass, open porosity included. It takes into account the shape of the particles and the roughness of their surface. The method of measuring the specific surface area is well known to those skilled in the art and widely documented in reference works. The specific area of a solid, in this case the bulking agent, is determined after degassing, by adsorption of a monolayer of gas, by Van Der Waals bonding, around each particle and in each open pore of the sample. The results obtained are exploited according to the equation established by Brunauer, Emmet and Teller.

The specific surface area of the sweetening composition according to the invention is determined by means of an SA3100-type Beckman-Coulter specific surface area analyzer, based on a test for absorption of nitrogen onto the surface of the product subjected to the analysis, by following the technique described in the article BET Surface Area by Nitrogen Absorption by S. Brunauer et al. (Journal of American Chemical Society, 60, 309, 1938).

The BET analysis is carried out in three points.

By definition, the specific surface area (Ss), also called "specific area", represents the total surface area (As) per unit of mass (M) and is generally expressed in $m^2/g$.

The specific surface area denotes the actual surface area of an object, as opposed to its apparent surface area.

According to one preferential mode of the invention, the chewing gum composition is characterized in that the bulking agent has a specific surface area, determined by the BET method, of less than 0.5 $m^2/g$, preferably of between 0.2 and 0.45 $m^2/g$, and preferably between 0.1 and 0.3 $m^2/g$, said specific surface area being measured on a fraction from 250 μm to 841 μm.

According to this preferential mode, the bulking agent, before being subjected to an analysis of its specific surface area, undergoes sieving on sieves of which the particle size is between 250 µm and 841 µm. This makes it possible to remove all the particles of which the diameter is less than 250 µm and also the particles of which the diameter is greater than 841 µm.

This consequently makes it possible to concentrate on the particle size fraction relating to the major distribution of the powders of bulking agent and to dispense with the fines and the particles that are too coarse, which would distort the analysis.

Another characteristic parameter of the chewing gum composition is that it comprises a bulking agent which preferably has a porosity of less than 0.0085 ml/g, preferably less than 0.0080 ml/g and even more preferentially less than 0.0070 ml/g.

In the present application, the term "porosity" is intended to mean all the gaps (pores) constituting the pulverulent bulking agent, these gaps being filled with fluids (liquid or gas). It is a physical parameter which conditions the flow and retention capacities of a substrate.

The porosity is also a numerical value defined as the ratio of the volume of gaps to the total volume of a porous medium.

$$\varphi = \frac{V_{pores}}{V_{total}}$$

with:
φ the porosity,
$V_{pores}$ the pore volume, and
$V_{total}$: the total volume of the bulking agent, i.e. the sum of the volume of solid and of the pore volume.

According to one embodiment of the invention, the chewing gum composition according to the invention is characterized in that the bulking agent is between 30% and 70%, preferably between 40% and 60%, and even more preferentially between 45% and 55%, the percentages being expressed by weight relative to the total weight of the chewing gum composition used.

According to the invention, the term "bulking agent" is intended to mean any pulverulent composition chosen from non-cariogenic carbohydrates other than maltitol, and/or fibers and/or monosaccharides and/or any mixtures thereof.

According to one preferential mode of the invention, the chewing gum composition is characterized in that the bulking agent is chosen from non-cariogenic carbohydrates other than maltitol.

According to this same preferential mode, the chewing gum composition according to the invention is non-cariogenic.

In the present invention, the term "non-cariogenic" is intended to mean chewing gum compositions which do not produce caries when they are consumed.

More specifically, the chewing gum compositions according to the invention lead to less acidification by the bacteria of the mouth than chewing gum compositions containing conventional sugars such as sucrose, glucose or fructose.

The non-cariogenic effect is in fact due to the presence, in the buccal cavity, of a large number and of a large variety of bacteria, in particular cariogenic bacteria (mutant streptococci in particular) which colonize the dental plaque (or dental film) and metabolize and ferment the sugars in foods, thereby leading to the production of acids, in particular lactic acid. Said acids allow a decrease in the peripheral pH of the tooth below the fateful pH of 5.7, the consequence of which is to dissolve the hydroxyl-apatite of the dental enamel and to create cavities therein. The tooth is then weakened since the high acidity causes demineralization (dissolution) of the dental enamel. The carie then progresses inside the tooth and reaches the pulp, causing pain.

Indeed, repeated consumption, and also a long residence time in the mouth, of foods rich in fermentable carbohydrates (containing sugar or sucrose, fructose, starch, etc.) form an environment conducive to the development of caries.

In the present invention, the term "non-cariogenic carbohydrate" is intended to mean all non-fermentable carbohydrates or non-acidogenic carbohydrates.

According to the present invention, the chewing gum composition is characterized in that the non-cariogenic carbohydrate is chosen from polyols, but also from non-fermentable monosaccharides that can be chosen from the group made up of isomaltulose, xylose, xylulose, allulose, arabinose, leucrose, tagatose, trehalulose and raffinose. Indeed, these carbohydrates are not capable of being converted into acids by fermentation, and therefore do not contribute to the formation of caries. These non-fermentable carbohydrates are not metabolized by the bacteria of the buccal cavity and do not cause acid production. There is therefore no decrease in pH in the mouth below the critical value of 5.7 and the cariogenic and erosive risks do not occur.

According to one preferential mode, the non-cariogenic carbohydrate is chosen from polyols and/or allulose and/or any mixtures thereof.

Thus, the chewing gum compositions according to the present invention satisfy the Sympadent [Toothfriendly] label.

From the point of view of confectionery manufacturers, a very clear desire also emerges. It is that of producing non-cariogenic confectionery products, i.e. confectionery products that do not cause tooth decay since the products that they contain do not produce acids and are not metabolized by the bacterial buccal flora.

Manufacturers are seeking to obtain confectionery products that satisfy the very strict specifications of the Association Sympadent Suisse [Swiss Toothfriendly Association], so as to be able to display on their confectionery the label known and recognized by all. This label, a small man in the form of a tooth with an umbrella, was created by Action Sympadent to denote dentition-friendly products and thus to serve as an indicator in the service of behavior that preserves the dentition. These products must be neither cariogenic nor erosive. Various types of sugars are cariogenic, which means that they are capable of causing caries. The detrimental erosive potential on the other hand depends on the acid content of a product.

Products bearing the Sympadent [Toothfriendly] label must first of all pass a scientific test known as the "measurement of the pH by telemetry". This test is performed by independent test centers. It is a normalized procedure in which the pH of dental plaque is measured on experimental subjects by placing electrodes covered with plaque in the interdental spaces. The measurement takes place during the consumption of the confectionery product to be tested and 30 minutes after its consumption. The confectionery product is considered to be non-cariogenic if the pH does not fall below the critical threshold of 5.7. The erosive potential is determined using an electrode without plaque placed in the saliva. The products that expose the teeth to less than 40 µmol of acid during their consumption are considered to be non-erosive.

The smiling tooth under its umbrella is an understandable symbol throughout the world. It is understood without further explanation. Products bearing it are tooth-friendly. This pictogram and the normalized indications of the nutritive values contribute to healthy food that is dentition-friendly. A consumer would rather be tempted to purchase confectionery products bearing this logo.

In one particularly preferential mode of the invention, the non-cariogenic carbohydrate is also sugar-free.

In one even more preferential mode, the non-cariogenic and sugar-free carbohydrate is chosen from polyols, and preferably from sorbitol.

In one even more preferential mode, the carbohydrate is sorbitol.

The applicant has in the past concentrated its efforts on the development of a novel sorbitol with a low specific surface area, that may also be suitable in the chewing gum compositions according to the invention.

The applicant has in fact protected, in application FR 14 56288, a sweetening composition characterized in that it has from 80% to 95% by dry weight of crystalline pulverulent sorbitol, an enthalpy at most equal to 150 J/g, and a volume mean diameter of between 200 and 350 µm. The sweetening composition is also characterized in that it has a specific surface area, determined according to the BET method, of less than 0.6 m$^2$/g, preferably of between 0.15 and 0.4 m$^2$/g, and even more preferentially between 0.20 and 0.35 m$^2$/g.

This sweetening composition protected in patent application FR 14 56288 by the applicant, having a purity of less than 95% by dry weight of sorbitol, is perfectly capable of being part of the chewing gum compositions according to the present invention, owing to its low specific surface area.

Thus, in the present application, when the bulking agent is sorbitol, it preferably has a purity of greater than 95% by dry weight of sorbitol. When the bulking agent is a polyol other than sorbitol, the purity will be between 80% and 99.9% by dry weight of polyol.

When the bulking agent contained in the chewing gum composition according to the invention is a polyol, it is also characterized by its particular mean particle size.

For the purposes of the present invention, the term "mean particle size" is intended to mean a mean particle diameter which is low and less than 350 micrometers. These values are determined using an LS 230-type laser diffraction particle size analyzer from the company Beckman-Coulter, equipped with its (dry process) powder dispersion module, according to the operating guide and the specifications of the manufacturer. The operating conditions of hopper screw speed and of vibration intensity of the dispersion chute are determined in such a way that the optical concentration is between 4° and 12°, ideally 8°. The measuring range of the LS 230-type laser diffraction particle size analyzer is from 0.04 µm to 2000 µm. The results are calculated as % by volume, and expressed in µm. The particle size distribution curve also makes it possible to determine the value of the volume mean diameter (arithmetic mean) D4,3.

The applicant has in fact noted that, when chewing gum compositions contain a bulking agent of polyol type having a high specific surface area, in particular at least greater than 1 m$^2$/g, it is advisable to use powders of polyols having a volume mean diameter (arithmetic mean) D4,3 of greater than 100 microns, but less than 350 microns. This is because the use of a polyol which has a high specific surface area and a high particle size may, when it is used in chewing gum compositions, give the sensation of a sandy and therefore unpleasant texture.

According to one preferential mode of the present invention, the applicant has also noted that, for specific surface areas that are low and therefore less than 0.5 m$^2$/g according to the BET method, it is preferable for the volume mean diameter (arithmetic mean) D4,3 of the bulking agent of polyol type, and preferably sorbitol, to be between 200 and 350 µm.

In one preferential mode, the volume mean diameter (arithmetic mean) D4,3 of the bulking agent of sorbitol type is between 250 and 350 µm or more preferentially between 280 and 330 µm.

The choice of the particle size of the polyol powders, in particular of the sorbitol powders, is very important. The sorbitol particles have a dendritic microscopic structure, i.e. like an entanglement of needles. Because of this particular structure, it has generally been noted that the use of sorbitol powder having a mean particle size of greater than 200 micrometers in the production of tablets, bars and/or chewing gums confers on said products a "sandy" texture, in particular on chewing gums (in particular during chewing).

The use of a bulking agent of sorbitol type in the production of the chewing gum compositions according to the invention, although it has a larger particle size (a mean particle size greater than 200 µm), has no negative effect on the organoleptic properties of the chewing gums. Indeed, as demonstrated hereinafter, the chewing gums produced using this bulking agent do not exhibit this unpleasant sandy texture in the mouth.

Sugar-free chewing gum is today number one in the sales, with a 90% market share in most European countries. By virtue of polyols, the chewing gums are non-cariogenic, contain less calories and have an excellent taste.

The trend toward a healthier diet is continuing to gain ground and is significantly modifying modes of consumption and purchasing habits. Eating less sugar while continuing to afford themselves indulgences is the desire of an ever-increasing number of consumers in response to the numerous nutritional recommendations. The use of sugar substitutes as a replacement for sugar is justified for the production of food products of reduced energy value, non-cariogenic foodstuffs and foods with no added sugar, and also for the production of dietetic products.

In the present invention, the term "polyols" denotes the products obtained by catalytic hydrogenation of simple reducing sugars which therefore have a DP equal to 1 (DP=degree of polymerization), but also of more complex reducing sugars composed of the higher homologs, having a DP of greater than or equal to 2, of these simple sugars, such as disaccharides, oligosaccharides and polysaccharides and also mixtures thereof. Generally, the simple reducing sugars that are intended for catalytic hydrogenation in order to obtain the compositions of polyols of the type of those of the invention are glucose, xylose, fructose and mannose. The polyols obtained are then sorbitol, xylitol and mannitol. The disaccharides are most commonly maltose, maltulose, isomaltulose and lactose, which produce, by hydrogenation, isomalt, isomaltitol and lactitol. The oligosaccharides and polysaccharides, which are higher molecular weight products, normally come from acid and/or enzymatic hydrolysis of starches and/or of potato flours, of xylans or of fructans such as inulin, but can also be obtained by acid and/or enzymatic recombination of monosaccharides or disaccharides such as those mentioned above.

Consequently, the term polyol denotes, in the present invention, a polyol chosen in particular from the group comprising sorbitol, xylitol, erythritol, isomalt, isomaltitol, lactitol, alpha-D-glucopyranosyl-1,6-sorbitol (=1,6-GPS), alpha-D-glucopyranosyl-1,1-mannitol (=1,1-GPM), alpha-D-glycopyranosyl-1,1-sorbitol (=1,1-GPS) and mixtures thereof.

In a secondary embodiment of the invention, the bulking agents consist of non-fermentable monosaccharides which can be chosen from the group made up of isomaltulose, xylose, xylulose, allulose, arabinose, leucrose, tagatose, trehalulose and raffinose.

In another embodiment of the invention, the bulking agents can also consist of fermentable monosaccharides which can be chosen from the group made up of glucose, fructose, galactose, maltose, sucrose, lactose and maltotriose.

In another embodiment of the invention, the bulking agents can also be chosen from soluble fibers, insoluble fibers and any mixtures thereof.

According to one preferential embodiment, the fibers are soluble and chosen from the group made up of fructans, including fructooligosaccharides (FOSs), oligofructose and inulin, glucooligosaccharides (GOSs), galactooligosaccharides (Gal-OSs), isomaltooligo-saccharides (IMOs), trans-galactooligosaccharides (TOSs), xylooligosaccharides, lactosucrose, pyro-dextrins, polydextrose, branched maltodextrins, indigestible dextrins, fiber-rich dextrins, and hydrogenated oligosaccharides and polysaccharides.

The term "soluble fiber" is intended to mean water-soluble fibers. The fibers can be assayed according to various AOAC methods. By way of example, mention may be made of AOAC methods 997.08 and 999.03 for fructans, FOSs and inulin, AOAC method 2000.11 for polydextrose, AOAC method 2001.03 for assaying the fibers contained in branched maltodextrins and indigestible dextrins, or AOAC method 2001.02 for GOSs.

According to one preferential mode, the sole source of fiber is made up of branched maltodextrins.

The term "branched maltodextrins" (BMDs) is intended to mean the specific maltodextrins identical to those described in patent EP 1 006 128-B1, of which the applicant is the proprietor. These BMDs have the advantage of representing a source of indigestible fibers beneficial for the metabolism and for intestinal equilibrium. In particular, use may be made of BMDs which are characterized in that they contain:

between 15% and 50% of 1,6-glucosidic bonds, preferentially between 22% and 45%, more preferentially between 20% and 40%, and even more preferentially between 25% and 35%, a reducing sugar content of less than 20%, preferentially of between 2% and 20%, more preferentially between 2.5% and 15%, and even more preferentially between 3.5% and 10%, a polydispersity index of less than 5, preferentially of between 1 and 4, more preferentially between 1.5 and 3, and a number-average molecular weight Mn of less than 4500 g/mol, preferentially of between 400 and 4500 g/mol, more preferentially between 500 and 3000 g/mol, more preferentially between 700 and 2800 g/mol, even more preferentially between 1000 and 2600 g/mol.

In particular, use may be made of BMDs containing between 15% and 35% of 1,6-glucosidic bonds, a reducing sugar content of less than 20%, a weight-average molecular weight $M_w$ of between 4000 and 6000 g/mol and a number-average molecular weight $M_n$ of between 250 and 4500 g/mol.

Some subfamilies of BMDs described in the abovementioned application can also be used in accordance with the invention. These are for example high-molecular-weight BMDs having a reducing sugar content at most equal to 5 and an Mn of between 2000 and 4500 g/mol. Low-molecular-weight BMDs have a reducing sugar content of between 5% and 20% and a molecular weight Mn of less than 2000 g/mol can also be used.

According to another embodiment, the bulking agents can be made up of a mixture of polyols and monosaccharides which are fermentable.

The applicant has to its credit noted that the use of a bulking agent other than maltitol having a low specific surface area, i.e. less than 0.5 $m^2/g$, measured on a fraction of 250 µm to 841 µm, makes it possible to produce a chewing gum composition having a not insignificant reduction in gum base.

The applicant company has demonstrated that the use of a bulking agent having a low specific surface area according to the invention is of particular advantage in terms of reducing the formulation costs in a chewing gum recipe.

This low specific surface area in fact makes it possible to produce chewing gums of which the volume in the mouth perceived by the consumer has been judged to be similar to a conventional chewing gum, although the chewing gum according to the invention comprises 30% by weight less gum base in its recipe.

Thus, according to the invention, said chewing gum composition is characterized in that the amount of gum base is reduced by 60%, preferably by 50%, and more preferably by 40%, relative to the amount of gum base compared with a prior art or conventional chewing gum composition, without having an impact on the final organoleptic qualities of the final product, and in particular the volume perceived during chewing and the aromatic intensity.

What is more, said chewing gum composition is also characterized in that the amount of flavorings is not insignificantly reduced. This is because putting less gum base in the recipe has a direct impact on the amount of flavorings to be added.

Thus, said chewing gum composition is characterized in that the amount of flavorings is reduced by 50%, preferably by 40%, and more preferably by 25%, relative to the amount of flavorings of a prior art or conventional chewing gum composition.

According to the invention, the flavoring or flavoring agent can comprise natural and/or synthetic compounds. It may in particular be mint, cinnamon, orange, lemon, or lime or flavorings corresponding to other fruits or plants, such as for example apple, strawberry, banana, cherry or fruit mixture flavorings. The flavoring agent may be in the form of a single product or in two or more different physical forms essentially comprising the same flavoring compounds. Several flavoring agents of different natures and in identical or different physical states can also be used.

Food acids can also be added to the composition in accordance with the invention, for example as taste enhancers, in low contents, in particular when a fruity flavoring is used.

In the present invention, the term "chewing gum" is used without implied distinction to denote chewing gums and bubble gums. The difference between these two types is, moreover, quite vague. It is customary to say that chewing gums are chewed whereas bubble gums are intended for making bubbles, and are thus conventionally rather consumed by young consumers.

Most chewing gums, whether they are with or without sugar, and sweet-coated or not, essentially comprise a water-insoluble gum base, hydrosoluble sweetening agents provided in liquid and/or pulverulent form and flavorings. They often comprise other ingredients, such as colorants, emulsifiers, plasticizers, intense sweeteners, water, etc.

The gum base is the ingredient which differentiates chewing gums from other confectionery products. This elastic substance has the property of being able to be chewed for hours without any substantial changes to its texture being induced. It does not disintegrate during chewing either. The gum base is a very important ingredient in the production of the centers. It varies as a function of the final product, chewing gum or bubble gum, of the format in sticks or tabs, with or without sugar, etc. Gum bases are nowadays really very different than those used in the past. They contain synthetic elastomers, plasticizers, softeners or softening agents, texturing agents and emulsifiers and also a variety of specific ingredients that will give the product its particular properties as a function of the final application.

The gum base constituting the chewing gum composition according to the invention is preferably ordinary and similar to those that are commonly used. It can also comprise synthetic and/or natural elastomers such as polyisoprene, polyvinyl acetate, polyisobutylene, latexes, resins such as terpenic resins, polyvinyl alcohols and esters, fats or waxes, for instance lanolin, partially hydrogenated or non-hydrogenated vegetable oils, fatty acids, partial glycerol esters, paraffin, microcrystalline waxes, bulking agents such s talc, calcium carbonate, elastomer plasticizers such as glyceryl triacetate, glyceryl monostearate, rosin derivatives, emulsifiers such as lecithin, sorbitol esters, colorants or whitening agents, antioxidants, and non-stick agents such as mannitol.

The applicant company has in particular succeeded in demonstrating that the use of a bulking agent according to the invention, i.e. a bulking agent other than maltitol having a low specific surface area, less than 0.5 $m^2/g$, measured on a fraction of 250 µm to 841 µm, in a chewing gum formulation makes it possible to confer on the chewing gum a final texture that is more flexible than that of the chewing gums obtained according to the same recipe but using bulking agents having a higher specific surface area.

Given that it is the gum base that to a large extent makes it possible to confer the texture on the chewing gum, the applicant company therefore had the idea of reducing the amount of gum base in such a way as not to modify the final texture of the chewing gum. The use of the bulking agent according to the invention also makes it possible to reduce the amount of flavorings conventionally used. This is because a part of the flavorings remains trapped in the gum base during chewing and these flavorings are thus never released into the saliva.

The advantage of the use of a bulking agent having a low specific area, i.e. less than 0.5 $m^2/g$, measured on a fraction of 250 µm to 841 µm, is therefore a double advantage since it makes it possible, on the one hand, to reduce the gum base content, thereby consequently making it possible to decrease, on the other hand, the amount of flavorings used. Such decreases in amount of gum and of flavorings bring about a considerable reduction in the production costs, and are therefore very advantageous for manufacturers.

The particular properties of the bulking agent used confer the ability to soften the gum base and therefore in the end the chewing gum.

Moreover, although the chewing gum composition according to the invention has a lower amount of flavorings in the recipe, the perception of the flavorings, both in terms of intensity and in terms of persistence, in the chewing gum composition according to the invention is at least identical to the chewing gum according to the prior art.

The applicant company has in particular demonstrated that, by reducing the gum base, it is entirely possible to obtain chewing gums that are entirely satisfactory in terms of texture. This was not at all obvious since the proportions of the various constituents are generally fixed and it is not possible to modify them without having a negative impact on the final quality of the products.

According to one preferential mode, the chewing gum composition according to the invention is characterized in that it comprises:
  from 10% to 28%, preferentially from 15% to 25%, and even more preferentially 20%, of at least one gum base,
  from 30% to 70%, preferably from 40% to 60%, and even more preferentially from 45% to 55%, of a bulking agent other than maltitol having a low specific surface area, i.e. less than 0.5 $m^2/g$, measured on a fraction of 250 µm to 841 µm,
  from 0.1% to 5%, preferentially from 0.5% to 3%, and even more preferentially from 1% to 1.8%, of at least one flavoring,
the percentages being indicated by dry weight relative to the total dry weight of said composition.

The applicant recommends carrying out this mixing at a temperature of between 45° C. and 80° C., preferably in a Z-arm mixer with a jacket or in a continuous mixer. Preferably, it is advisable to heat the gum base beforehand, to a temperature of between 45° C. and 80° C., preferably between 45° C. and 55° C., by any means known to those skilled in the art. By way of example, it will be possible to heat it in a microwave oven or in an oven.

The mixing of the abovementioned compounds may also use another polyol as sweetening agent, in powder or liquid form, such as, for example, mannitol, maltitol, xylitol, erythritol, lactitol, isomalt, maltitol syrups, sorbitol syrups or hydrogenated glucose syrups.

The mixing of the abovementioned compounds may also use, in an amount of at most 5% by weight relative to the total weight of the chewing gum, at least one constituent chosen from colorants, intense sweeteners such as aspartame, acesulfame-K, alitame, neotame, sucralose, saccharin, neohesperidin DC, steviosides, brazzein, etc., pharmaceutical active agents, minerals, plant extracts, antioxidants, and indigestible fibers such as, for example, oligosaccharides such as fructooligosaccharides, indigestible fibers such as Fibersol™ sold by the company Matsutani, or else Nutriose® sold by the applicant, emulsifiers, such as lecithin, etc.

The gum base used may be adapted to the type of chewing gum produced. It may comprise synthetic and/or natural elastomers, such as polyisoprene, polyvinyl acetate, polyisobutylene, latexes, resins such as terpenic resins, polyvinyl alcohols and esters, fats or waxes, such as, for example, lanolin, partially hydrogenated or non-hydrogenated vegetable oils, fatty acids, partial glycerol esters, paraffin or microcrystalline waxes.

In the production of the chewing gum composition, the step of mixing the abovementioned ingredients is followed by steps of extrusion, rolling, cutting, cooling and then packaging, carried out according to any technique well known to those skilled in the art.

In the end, the chewing gum is present in one of the forms well known to those skilled in the art, such as sticks, balls, sweet-coated tablets, cubes or else tablets.

According to the invention, the ingredients and the gum base are mixed in a kneader for 15 to 20 minutes. At the end of blending, the paste reaches a temperature of approximately 50° C. The chewing gum paste is then poured into an extruder. Once correctly pressed, it then forms more or less thick strips. The strips then pass through the roller and are cut into sticks or cores. After cooling, the sticks or cores of sweet-coated tablets are maintained at a precise temperature and humidity for 6 to 48 hours. This phase is carefully controlled, since the quality of the chewing gums is dependent thereon.

According to one variant of the invention, the chewing gum compositions of the present invention can be film-coated. The film-coating consists of the application of film-forming liquid composition which, after drying, becomes a protective film. This film-coating serves, for example, to protect the active ingredients contained in the confectionery product, to protect the confectionery product itself from humidity, impacts and friability, and also to confer on the confectionery products attractive visual properties: shine, uniform color, smooth surface, etc.

According to a more preferential variant, the compositions used for the film-coating are those described in patent application WO 2005/060944, of which the applicant is the proprietor.

According to another preferential mode, the chewing gum compositions of the present invention can in addition, when it is possible, be filled with liquid, pasty, solid, powdered, etc. fillings. They can also be coated with chocolate, sweet-coated, candied, frosted, etc.

According to another embodiment of the invention, the chewing gum composition may also optionally be sweet-coated. According to the invention, the sweet-coating step may be a soft sweet-coating or a "hard" sweet-coating.

Hard sweet-coating is a unitary operation used in a good number of fields, among which are those of the confectionery industry and the pharmaceutical industry. It can also involve the additive industry, namely flavorings, sweeteners, vitamins, enzymes, acids and plant-based products. This operation consists in creating a hard crystalline coating at the surface of solid or pulverulent products, in order to protect them for various reasons or else in order to make them attractive from a visual or taste point of view. Very generally, this unitary operation is carried out by placing such products, as a core to be coated, in a sweet-coating pan. Hard sweet-coating aims to obtain a crunchy and sweet layer, which is always very popular in the case of confectionery products or chewing gums. It always requires the use of a syrup and/or of a suspension containing crystallizable materials. The hard and crystalline coating is then obtained by applying this syrup or this suspension to the cores and evaporating the water introduced thereby by means of drying with hot dry air, thereby causing crystallization. This cycle must be repeated a very large number of times, about ten to twenty-four times, in order to obtain the desired degree of enlargement. The term "degree of enlargement" is commonly used to refer to the increase in weight of the products, considered at the end of the operation compared with the beginning, relating to the final weight of the products.

In the present invention, the hard sweet-coating can be preceded or followed by other coating techniques. The following techniques, which are often carried out also using a sweet-coating pan, can be retained:

gumming which is a technique in which syrups of materials which are non-crystallizable and generally non-hygroscopic are used, such as gums arabic, modified celluloses and starches, and maltodextrins. This technique makes it possible, after one or two applications of the gumming syrup to the product to be coated, to create a vitreous film which acts as a barrier against the migration of oxygen, water and fats. In this process, powders of various nature can also be used together with these non-crystallizable syrups, so as to fix the water introduced by the syrups. In yet other cases, sugars or polyols which are molten or liquefied with solvents are used. The hard, brittle, vitreous coating is then obtained by cooling or by evaporation of the solvents;

soft sweet-coating which consists in creating a very flexible and soft coating at the surface of the products. This coating is obtained by repeated applications, on the one hand, of a non-crystallizable syrup such as in general starch hydrolyzates, and, on the other hand, of a powder, in general of crystalline sucrose. The coating is usually thick. The degree of enlargement for this technique is about from 10% to 80%, or even more. It should be noted that the constituent material of the syrup is usually different than that of the powder;

brightening which consists, by using fatty substances or waxes generally introduced in crystalline form as flakes or in the form of alcoholic solutions, in coating the products with a very fine fatty film-coating in order to reduce water transfers from or to the coated products, but also to make their surface more attractive.

The term "hard sweet-coating" used in the present invention also comprises very similar techniques, namely glazing and frosting. Glazing consists of one or two applications or charges of crystallizable syrup that is dilute compared with that used in hard sweet-coating. The aim is often to perfect the surface appearance of sweet-coated products. Frosting, for its part, is also directed toward improving the appearance of the products, but also toward isolating them from atmospheric moisture. This technique resembles hard sweet-coating, in the sense that a crystallizable syrup is used. The essential difference lies in the fact that the number of cycles performed is only one, two or three.

Sweet-coating is a long and laborious process, including a large number of successive steps. Each of these steps, also known as the sweet-coating cycle, typically includes a phase of applying, generally by spraying, a sweet-coating syrup (containing one or more polyols, but also sometimes binders such as gum arabic or gelatin, colorants such as $TiO_2$, intense sweeteners, etc.) to the cores, a rotating phase for distribution of said syrup on the cores, also known as the waiting time, and a phase of drying each new layer of syrup performed by blowing with hot, dry air. This succession of cycles must be repeated a very large number of times, about ten to twenty-four times, so as to obtain the desired degree of enlargement. The thickness of the shell or degree of enlargement is chosen in particular as a function of the core to be sweet-coated or of the desired effects. Nowadays, the major preoccupation of chewing gum manufacturers is to obtain chewing gums that have a very crunchy hard layer, but while reducing the sweet-coating times.

During the first phase of production of the chewing gum centers, which consists in kneading all the ingredients included in the composition at a temperature of between 50° C. and 80° C., the liquid phase and the gum base coat the crystalline sweeteners and dissolve them to the point of saturation of the liquid phase. However, as the temperature decreases during the cooling process, the solubility of the polyols also decreases and the dissolved crystalline phase will partially recrystallize, thereby leading to hardening of the chewing gum. Thus, the role of the liquid phase is to control the recrystallization of the crystalline sweeteners so as to prevent excessive fragility or hardening of the chewing gums during production, but also during storage. If the anti-crystallization syrup contains a significant amount of dissolved polyols similar to those of the crystalline phase, the crystallization during the production process or during storage will take place and lead to chewing gums that are too fragile or too hard.

The water of the chewing gum may be provided in the form of free water or by other constituents.

The chewing gum composition according to the invention may comprise a binding agent, in a concentration of from 0.1% to 30%. This binding agent may be chosen preferably from water, glycerol, hydrogenated or non-hydrogenated mono-, di-, oligo- or polysaccharide syrups, and syrups of low-calorie bulking agents and any mixtures thereof.

The mono-, di-, oligo- or polysaccharide syrups may be, for example, xylitol, sorbitol, maltitol, lactitol, isomaltulose, hydrogenated isomaltulose, erythrose or erythritol syrups, syrups which are preferably hydrogenated, derived from the hydrolysis of starches or of inulins, containing oligosaccharides and/or polysaccharides. With regard to the syrups of low-calorie bulking agents, it is preferred in particular to select polydextrose, polyglucose or dextrin syrups.

According to one preferential embodiment, the chewing gum composition may contain up to 20% of a maltitol syrup.

By way of example, mention may be made of the maltitol syrups sold by the applicant under the brand name Lycasin®, such as Lycasin® 80/55 (75% of dry matter and 50-55% of maltitol dry matter) or Lycasin® 85/55 (85% of dry matter and 50-55% of maltitol dry matter). These ready-to-use anti-crystallization syrups or agents are particularly suitable for combined use with all the crystalline polyols mentioned below, and thus make it possible to give the chewing gum improved plasticity.

According to another embodiment, the invention also relates, in addition to the chewing gum compositions or chewing gum, to the use of a particular bulking agent in the production of tablets for pharmaceutical or food use.

Thus, the present invention also relates to the use of a bulking agent other than maltitol having a specific surface area, determined by the BET method, of less than 0.5 m$^2$/g, preferably of between 0.2 and 0.45 m$^2$/g, and preferably between 0.1 and 0.3 m$^2$/g, said specific surface area being measured on a fraction of 250 µm to 841 µm, in the production of chewing gums and/or in the production of tablets for pharmaceutical or food use.

The bulking agent content of the tablet will depend on the desired use of said tablet. Typically, the bulking agent content of the tablet may be between 1% and 90% by dry weight.

The invention will be understood more clearly on reading the following examples, which cannot in any way limit the present invention.

Example 1: Measurement of the Specific Surface Areas of Various Bulking Agents According to the Invention According to the invention, the specific surface area is measured either on the total powder constituting said bulking agent, or on a sample of powder obtained on a fraction of 250 µm to 841 µm.

Sample Preparation

To prepare the sample, it is necessary to sieve a sufficient amount of sample on sieves of 841 µm and 250 µm in order to recover approximately 3 grams of a particle size fraction of between 841 and 250 microns.

A test specimen sufficient to ¾-fill the reservoir of the cell is introduced into a measuring cell of the apparatus, previously dried and tared to within 0.001 g.

Degassing

The cell containing the sample is placed in the degassing station.

Said degassing is carried out by referring to the instructions for use of the apparatus.

Analysis of the Powder

Once the degassing has been carried out, the cell is re-weighed to within 0.001 g and placed in the measuring station. The analysis is carried out by referring to the instructions for use of the apparatus.

The apparatus automatically processes the results collected. The result is expressed in m$^2$/g.

TABLE 1

Measurements on product having undergone beforehand a fractioning on 250 µm to 841 µm

| Bulking agent | Specific surface area (in m$^2$/g) |
|---|---|
| Xylitol 90 | 0.20 |
| Particle size 100 µm | |
| Isomalt PF | 0.39 |
| Branched maltodextrins Nutriose FB06 | 0.21 |
| Allulose | <0.20 |
| Mannitol 60 | 0.25 |
| Anhydrous dextrose | <0.20 |
| Glucidex 19 | 0.25 |
| 2% starchy confectioners' sugar | 0.35 |
| Sorbitol suitable for the invention | 0.1 to 0.3 |

Example 2

Characteristics of a Bulking Agent of Sorbitol Type According to the Invention

Table 2 below reproduces the characteristics of a bulking agent of sorbitol type that can be used in the production of the chewing gum compositions according to the invention.

Said bulking agent is compared to a commercially available sorbitol powder sold by the applicant company under the brand name Neosorb®.

TABLE 2

Characteristics of a bulking agent of sorbitol type LabA

| | Bulking agent of sorbitol type: LabA | Neosorb ® P60W sorbitol |
|---|---|---|
| Sorbitol (%/dry) | 95.5 | 98.5 |
| Maltitol (%/dry) | 1.4 | 0.2 |
| Mannitol (%/dry) | 0.8 | 0.6 |
| Volume mean diameter (µm) | 320 | 290 |
| Specific surface area (m$^2$/g) | 0.3 | 0.85 |
| Porosity ml/g | 0.006 | 0.00136 |

Example 3

Chewing gum composition according to the invention prepared using the bulking agent of sorbitol type described in example 2 above.

The control was prepared with a sorbitol powder sold by the applicant company under the brand name Neosorb®, of Neosorb® P60W type.

All the percentages expressed are expressed relative to the total dry weight of the chewing gum composition used.

1. Preparation of the Chewing Gum Compositions

Ingredients used in the chewing gum compositions, table 3 below:

| Ingredients | Control chewing gum composition (%) | Chewing gum composition according to the invention (%) |
| --- | --- | --- |
| Solsona T gum base | 30 | 22 |
| Neosorb ® P60W sorbitol | 48.270 | 0 |
| Bulking agent of sorbitol type LabA | 0 | 48.693 |
| Lycasin ® 85/55 maltitol syrup | 4.83 | 14.00 |
| Mannitol 60, fine powder | 8 | 8 |
| Glycerol | 4 | 3 |
| Fresh mint liquid flavoring M0060167 | 1.4 | 1.073 |
| Mane menthol crystals | 0.5 | 0.383 |
| Fresh mint powder flavoring SDM0060167 | 2.2 | 2.2 |
| Acesulfame-K | 0.150 | 0.150 |
| Aspartame | 0.150 | 0.150 |
| Liquid sunflower lecithin-type emulsifier | 0.300 | 0.150 |
| TiO$_2$ powder | 0.2 | 0.2 |
| TOTAL | 100 | 100 |

The Solsona T gum base is sold by the company Cafosa.

The Neosorb® P60W sorbitol is a crystalline sorbitol powder, sold by the applicant. The mannitol 60, the xylitol 90 and the Lycasin® 85/55 maltitol syrup are also sold by the applicant.

All the flavorings are supplied by the company Mane et Fils.

Procedure for Preparing the Control Chewing Gum Compositions and Chewing Gum Compositions According to the Invention Mixing: Procedure in minutes—carried out in a Z-arm kneader at 45° C.—batch production of 50 kg of center 0 min: Introduce the molten gum base (stoved overnight at 50° C.) and the mannitol.

3 min: Add the Lycasin® 85/55.

5 min: Add the bulking agent, thus either the Neosorb® sorbitol or the sorbitol of LabA type.

9 min: Add the glycerol.

10 min: Add the mint powder flavoring and the flavoring of menthol crystal type.

12 min: Add the mint liquid flavoring.

15 min: Unload the kneader (the paste is at approximately 50° C.). Form cakes of approximately 2 kg and store them for 1 hour at 50% RH and at 20° C. The cakes must be at approximately 48° C. for the extrusion.

Extrusion (Togum TO-E82 machine)
Body setpoint temperature=36° C.
Head setpoint temperature=39° C.

4-station rolling-2-station precutting (Togum TO-W191 machine).

Sprinkling of the chewing gum strip with a 90/10 mannitol/talc mixture.

Maturation

Store the precut plaques of tabs at approximately 15° C.-50% RH for approximately 24 h.

2. Evaluation of the Organoleptic Qualities of the Chewing Gums

The chewing gums obtained above were tasted by a panel of 15 individuals trained in the tasting and grading of chewing gums.

The panel was asked to grade from 0 to 4 the flexibility of the chewing gums during the first seconds of chewing, but also after three minutes of chewing, 4 being the maximum flexibility and 0 corresponding to a very hard, or even brittle, chewing gum.

The panel was also asked to grade the perception of the flavor during chewing. This taste was also carried out during the first seconds of chewing and after three minutes of chewing in order to evaluate the persistence of the flavor, 4 being the grade given for a very strong flavor and 0 corresponding to a chewing gum no longer having any flavor at all.

The products were presented in random order, and coded with a 3-figure number so that the panelists are not influenced either by knowledge of the products or by their codes. The tastings were carried out in a sensory analysis laboratory.

At T+0, the chewing gum is placed in the buccal cavity and at the same time the timer is started. Chewing then begins.

The data were processed by statistical processing (Anova and mean comparison tests are performed on the means obtained at each time interval).

TABLE 4

Comparison of the flexibility and of the flavor persistence during chewing

| | Evaluation of flexibility | | Evaluation of flavor persistence | |
| --- | --- | --- | --- | --- |
| | T = 10 seconds | T = 3 min | T = 10 seconds | T = 3 min |
| Control CG | 4 | 3 | 4 | 2 |
| CG according to the invention | 4 | 3 | 4 | 3 |

It emerges that:

the flexibility of the two chewing gums changes in an identical manner. Although containing a smaller amount of gum base than the control chewing gum, no difference in terms of texture and more particularly in terms of flexibility between the two samples was noticed by the panel of tasters.

In terms of the perception and persistence of the flavor, here again there is no difference at T=10 seconds between the control chewing gum and the chewing gum according to the invention. Although having a lower amount of flavorings in the recipe, the perception of said flavorings in the chewing gum containing the sweetening composition according to the invention is identical to the control chewing gum. It would even appear that the flavor persistence is improved over time since the chewing gum obtained from the sweetening composition according to the invention, containing less gum base and less flavoring, is nevertheless graded as being slightly better than the control chewing gum after three minutes of chewing.

Thus, the chewing gum produced with the sweetening composition according to the invention and containing 8% less gum base relative to weight, that is to say a reduction in said gum base of 27%, and containing 0.44% less of flavoring relative to weight, that is to say a reduction of 23% in the amount of flavoring, is identical in terms of texture and is slightly better in terms of flavor persistence.

The advantage of a chewing gum composition according to the present invention is perfectly demonstrated by this example.

Example 4

Chewing gum compositions according to the invention prepared using various bulking agents capable of being included in said compositions All the percentages expressed are expressed relative to the total dry weight of the chewing gum composition used.

The various composition recipes are presented in table 6 hereinafter.

The control is a chewing gum composition prepared with a commercially available sorbitol powder sold by the applicant company under the brand name Neosorb®, but having a specific surface area at 0.5 m²/g and being the sorbitol generally used in the prior art.

the final organoleptic properties of the products obtained provided that a bulking agent having a low specific surface area is used.

All four of the compositions according to the invention exhibit a reduction in gum base of 8% relative to weight, that is to say a reduction of the latter of 27%, and a reduction in flavoring of 0.45% relative to weight, that is to say a reduction of 24% of the amount of flavoring.

This enables considerable economic savings without any negative impact on the product. This is what is currently sought by chewing gum producers.

The advantage of a chewing gum composition according to the present invention is perfectly demonstrated by this example.

The invention claimed is:

1. A chewing gum composition, comprising:
   at least one gum base and
   between 30% and 70% by weight of a bulking agent comprising sorbitol in a purity of greater than 95% by dry weight of sorbitol,
   said bulking agent having a specific surface area, determined by the BET method, of between 0.1 and 0.3 m²/g, said specific surface area being measured on a fraction of 250 μm to 841 μm, the percentages being expressed by weight relative to the total weight of the chewing gum composition wherein the amount of gum base is reduced relative to a chewing gum composition containing sorbitol having a specific surface area greater than 0.5 m²/gm.

| Bulking agent | Control composition | Confectioners' sugar | Dextrose | Fructose | Allulose |
|---|---|---|---|---|---|
| Ground allulose powder 125 microns | — | — | — | — | 61.90 |
| Confectioners' sugar | — | 62.05 | — | — | — |
| Dextrose | — | — | 62.05 | — | — |
| Fructose | — | — | — | 62.05 | — |
| Neosorb ® P60W sorbitol | 59.6 | — | — | — | — |
| Solsona T gum base | 30 | 22.00 | 22.00 | 22.00 | 22.00 |
| Glycerol | 1 | 1.00 | 1.00 | 1.00 | 1.00 |
| Glucose syrup containing 83% DM | 7.5 | 13.50 | 13.50 | 13.50 | 13.50 |
| Liquid mint flavoring | 1.3 | 0.95 | 0.95 | 0.95 | 0.95 |
| Powdered mint flavoring | 0.6 | 0.50 | 0.50 | 0.50 | 0.50 |
| Aspartame | — | — | — | — | 0.15 |
| TOTAL | 100 | 100 | 100 | 100 | 100 |
| % reduction of gum base | — | | | | |
| relative to weight | | 8 | 8 | 8 | 8 |
| relative to gum base | | 27 | 27 | 27 | 27 |
| % reduction of flavorings | — | | | | |
| relative to weight | | 0.45 | 0.45 | 0.45 | 0.45 |
| relative to gum base | | 24 | 24 | 24 | 24 |

The process for preparing the chewing gum centers is such as that described in the previous example.

The chewing gums obtained above were tasted by a panel of 15 individuals trained in the tasting and grading of chewing gums.

The flexibility and the aromatic perception were graded according to the same protocol as that described in the previous example.

All the chewing gums tasted exhibited a satisfactory flexibility and an identical aromatic perception.

Thus, it is entirely possible to prepare chewing gum compositions having a reduced amount of gum base and a reduced amount of flavorings, without having an impact on 2. The chewing gum composition according to claim 1, wherein the bulking agent has a porosity of less than 0.0085 ml/g.

3. The composition according to claim 1, wherein said bulking agent is present in an amount of between 40% and 60% by weight relative to the total weight of the chewing gum composition.

4. The composition according to claim 1, further comprising as an additional bulking agent a pulverulent composition comprising at least one of non-cariogenic carbohydrates, fibers and monosaccharides.

5. The composition according to claim 4, wherein said non-cariogenic carbohydrates are selected from at least one of polyols and allulose.

6. The composition according to claim 5, wherein the additional bulking agent is selected from the group consisting of at least one of xylitol, erythritol, isomalt, isomaltitol, lactitol, alpha-D-glucopyranosyl-1,6-sorbitol (=1,6-GPS), alpha-D-glucopyranosyl-1,1-mannitol (=1,1-GPM), and alpha-D-glucopyranosyl-1,1-sorbitol (=1,1-GPS).

7. The chewing gum composition according to claim 1, comprising:
   the at least one gum base in an amount of from 10% to 28%,
   the bulking agent in an amount of from 40% to 60%, and
   at least one flavoring in an amount of from 0.1% to 5%,
   the percentages being indicated by dry weight relative to the total dry weight of said composition.

8. The chewing gum composition according to claim 1, wherein the sorbitol is in powder form.

9. The chewing gum composition according to claim 1, wherein the sorbitol is crystalline sorbitol.

10. The chewing gum composition according to claim 9, wherein the sorbitol has a dendritic microscopic structure.

* * * * *